United States Patent [19]

Levert et al.

[11] Patent Number: 4,722,610

[45] Date of Patent: Feb. 2, 1988

[54] MONITOR FOR DEPOSITION ON HEAT TRANSFER SURFACES

[75] Inventors: Francis E. Levert; James C. Robinson; Jerry Golden, all of Knox County, Tenn.

[73] Assignee: Technology For Energy Corporation, Knoxville, Tenn.

[21] Appl. No.: 837,379

[22] Filed: Mar. 7, 1986

[51] Int. Cl.[4] .................. G01K 17/00; G01N 25/20
[52] U.S. Cl. ........................................ 374/43; 374/29; 110/185; 122/379
[58] Field of Search ................ 110/185; 122/379, 392, 122/504.2; 374/29, 43, 44, 103, 107, 181

[56] References Cited

U.S. PATENT DOCUMENTS

| | | | |
|---|---|---|---|
| 2,986,935 | 6/1961 | Cupido et al. | 374/181 |
| 3,256,734 | 6/1966 | Storke, Jr. | 374/43 |
| 3,257,993 | 6/1966 | Kochey, Jr. | 122/392 |
| 3,724,267 | 4/1973 | Zoschak | 374/30 |
| 4,097,341 | 6/1978 | Schell et al. | 374/43 |
| 4,126,042 | 11/1978 | Lynch | 374/181 |
| 4,309,901 | 1/1982 | Rolinski et al. | 374/29 |
| 4,383,438 | 5/1983 | Eaton | 374/7 |
| 4,488,516 | 12/1984 | Bueters et al. | 122/379 |
| 4,514,096 | 4/1985 | Wynnyckyj et al. | 374/27 |
| 4,527,908 | 7/1985 | Arisi | 374/147 |
| 4,603,660 | 8/1986 | Wynnyckyj et al. | 122/379 |

FOREIGN PATENT DOCUMENTS

| | | | |
|---|---|---|---|
| 1391826 | 2/1965 | France | 374/29 |
| 1403950 | 8/1975 | United Kingdom | 374/30 |
| 1423830 | 2/1976 | United Kingdom | 374/30 |
| 161544 | 3/1964 | U.S.S.R. | 374/44 |

OTHER PUBLICATIONS

S. B. H. C. Neal et al, "The Measurement of Radiant Heat Flux in Large Boiler Furnaces-II Development of Flux Measuring Instruments", *International Journal of Heat and Mass Transfer*, vol. 23, pp. 1023-1031, Great Britain 1980.

Primary Examiner—Charles Frankfort
Assistant Examiner—W. Morris Worth
Attorney, Agent, or Firm—Pitts and Brittian

[57] ABSTRACT

A monitor for determining a buildup of slag on the flame side of water cooled walls of coal fired steam generators and other heat transfer surfaces. This monitor has a body to be positioned in an orientation similar to the water tubes of the steam generator (or other heat transfer surfaces) so that any deleterious buildup on the surfaces will also be effected upon the exterior of the monitor. Positioned within the body of the monitor is a temperature sensor, such is a thermocouple having at least a hot junction. Also positioned within the body and proximate the sensor (e.g., thermocouple) is a heater unit having a high temperature portion located proximate the hot junction. In this manner, when the heater is energized, the hot junction is raised to a preselected temperature. By monitoring the time constant of temperature change of the sensor with current to the heater being cycled, information as to the degree of buildup on the exterior of the body can be obtained. Accordingly, deposit removing equipment of conventional type can be operated when the buildup has reached a point where a change in the heat exchange qualities of the surface has become ineffective. Additional temperature sensors (e.g., thermocouples) can be used to provide temperature information from which instantaneous heat flux can be computed.

10 Claims, 4 Drawing Figures

MONITOR FOR DEPOSITION ON HEAT TRANSFER SURFACES

DESCRIPTION

TECHNICAL FIELD

This invention relates generally to devices for monitoring the effectiveness of heat transfer surfaces, and more particularly to a device for monitoring the slag deposition on the exterior of boiler tubes of steam generators and the like, and the effectiveness of slag and soot removal systems.

BACKGROUND OF THE INVENTION

The fouling of heat transfer surfaces due to the deposition of slag and other constituents of fly ash is a major problem facing the operators of coal fired steam generators. Reduction of heat transfer coefficients on the outer surface of boiler tubes changes the heat distribution within the furnace and reduces overall boiler efficiency. Continued increase of the fouling will eventually reduce the units' generating capability. In addition, ash and slag deposition results in increased velocities and pressure drops in the convective regions of steam generators, thus potentially increasing erosion and auxiliary power consumption. Furthermore, this accumulation often accelerates metal corrosion because of the coatings' chemical composition.

In order to minimize the effect of slag deposition, soot blowers are employed at both the furnace wall and in the convective regions of the steam generator. These soot blowers direct controlled jets of high energy compressed air or superheated steam against the surfaces to mechanically remove the slag and ash deposits. Currently, soot blowers are either operated on a varying time-actuated cycle, or they are turned on manually based upon the operator's perception of the need to clean the furnace. Both of these methods are inadequate. Because the conditions of the furnace fluctuate widely, a time actuated sequence may or may not be effective in removing the slag and soot on the one hand or, if they are operated too frequently, unnecessary energy is expended. The same problems exist if there is manual operation based upon an operator's perception of the need to clean the furnace.

Several slag (ash) and heat flux monitors have been developed toward solving the problem of determining slag buildup and the measuring of heat flux in boiler furnaces. Typical of the ash monitoring systems is described in Trans. of the ASME Il. of Engr. for Power, Vol. 103, p. 532 (July 1981). An article describing a heat flux monitor appears in Int. J. Heat Mass Transfer, Vol 23, p. 1023 (1980). Both of these monitors (and others known in the art) utilize thermocouples for determining temperatures. None, however, provide for an active method of directly determining the surface condition of the monitor.

Accordingly, it is a principal object of the present invention to provide a means for directly monitoring the condition of heat transfer surfaces and activating a removal system only when such would be of significant benefit.

It is another object of the present invention to provide means for operating soot blowers and the like within furnaces only under absolutely needed conditions thereby reducing corrosion and erosion of the surfaces, and in particular, tube walls.

It is also an object of the present invention to provide a device for monitoring the effective heat transfer of a heat transfer surface and thus the surface condition of the monitor.

These and other objects of the present invention will become apparent upon a consideration of the following drawings and reference to the detailed description which follows.

DISCLOSURE OF THE INVENTION

According to the present invention, there is provided a device for mounting proximate the heat transfer surfaces of a coal fired steam generator or the like, such that the exterior surface thereof is subjected to the same environment as the heat transfer surfaces. One or more temperature sensor units are utilized to provide information as to the temperature, and thus the condition, of the heat transfer surface and the body of the present invention. One of the sensor units is mounted in the body of the device which can act as a absolute temperature monitor for the device. If this sensor is a thermocouple of the differential type, at least some of the natural temperature fluctuations of the furnace are compensated for in the output signal. Mounted adjacent to this first sensor is a heater unit whereby current passing through the heater creates a region of high temperature proximate the active portion of the sensor. When the heater is activated, the response time of the adjacent temperature sensor is used to determine the presence or lack of slag on the surface of the device. When the heater is deactivated, the rate of change of the temperature of the sensor can also be used as a measure of the surface condition. In this manner the slag and other detrimental buildup can be monitored to determine the appropriate (economic and effective) time for operation of soot removers and the like to return the heat transfer surface to a relatively higher degree of heat transfer. Other temperature sensors of the monitor can be positioned to provide signals corresponding to the temperatures of the body of the monitor and the water wall, respectively. Also, if the spacing between these sensors is known, their output signals can be used to determine the instantaneous heat flux at the location of the monitor within the boiler.

BEST MODE FOR CARRYING OUT THE INVENTION

Figure 1:
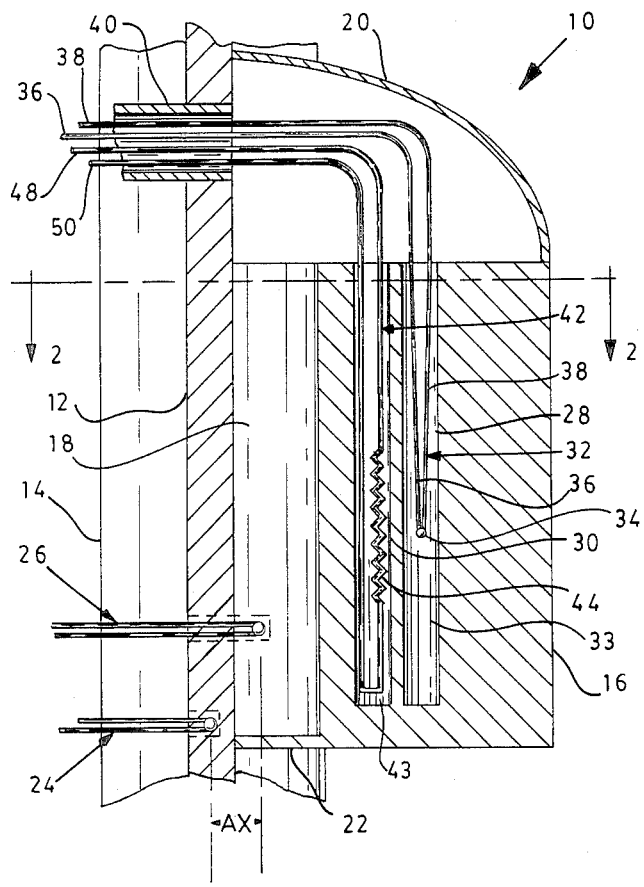
FIG. 1 is a longitudinal cross-section of a device according to one embodiment of the present invention. This cross-section taken at 1—1 of FIG. 2.
Figure 2:
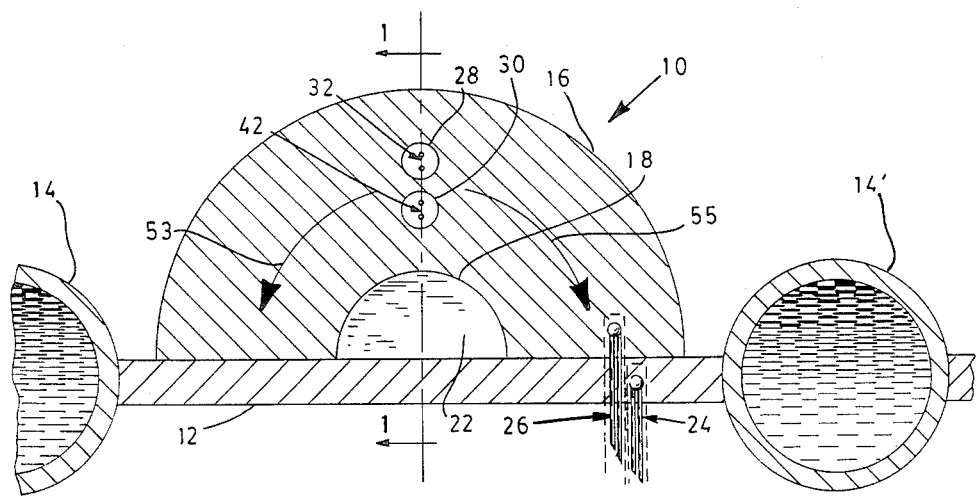
FIG. 2 is a transverse cross-section of the device of the present invention taken at 2—2 of FIG. 1.

Referring to FIGS. 1 and 2, shown generally at 10 therein is a monitor for slag deposition. The elements of the monitor are not drawn to exact geometrical proportions, rather they are shown only to illustrate the essential components. Shown in these figures is a water wall 12 which connects between boiler tubes 14 having water flowing therethrough. The monitor 10 has a semi-cylindrical body 16 formed with an axially located semi-cylindrical air-filled volume or bore 18. The air space 18 acts to thermally decouple the central portion of the body 16 from the water wall 12 thereby causing thermal energy incident upon the monitor to flow through the narrow legs of the body to the wall. For purposes described hereinafter, this body can be attached to the wall 12 in any suitable manner as by bolting, welding, or the like, with the body 16 being oriented toward the flame within a boiler. Attached to, and covering, the top of the body 16 is a cover 20, and the lower end of the bore 18 is closed, as at 22.

There typically is one temperature sensor 24 typically a thermocouple embedded in the water wall 12, and a second sensor (thermocouple) 26 inserted into the body 16 near the water wall. These are intended for providing information as to the absolute temperature of these bodies as well as the instantaneous heat flux within the boiler at the location of the monitor.

The body 16 of the monitor 10 is provided with cylindrical channels as at 28, 30, that are in close proximity. Channel 28 contains a thermocouple 32 (or other suitable temperature sensor) having a junction 34. Junction 34 is at the extremity of leads 36, 38 which are connected to appropriate circuitry (see FIG. 3). These thermocouple leads pass through any appropriate conduit, such as illustrated at 40, for conveyance to the circuitry. Although not shown in this figure, the thermocouple 32 is contained within appropriate thermal insulation as at 33. Furthermore, although shown schematically, this thermocouple 32 would be a conventional sheathed thermocouple such as is well known in the art.

The second channel 30 serves as a housing for a heater unit 42. This heater unit has a high temperature portion 44 positioned proximate the junction 34 of the thermocouple 32. Although shown schematically, this heater unit 42 would typically be a sheathed heater unit filled with insulation as at 43 having the desired heater portion. Such heater is well known to those versed in the art. Low resistance leads 48, 50 from the heater 42 also pass out through the conduit 40 for connecting to appropriate circuitry.

In this embodiment, the thermocouple 32 (thermocouple 52 in the embodiment of FIG. 3) is positioned on the side of the body 16 toward the boiler flame relative to the heater 42. This is deemed to be the preferred orientation; however, the positions can be interchanged or they can be rotated 90 degrees from the positions shown if they are in close proximity.

Both the sheathed thermocouple 32 and the sheathed heater 42 must be in good thermal contact with the body 16 of the monitor 10. This can be accomplished during construction of the monitor in several ways. For example, the thermocouple and heater units can be installed in their closely fitting channels 28,30 and the body 16 then swaged against the sheaths of the thermocouple and heater. Alternatively, the channels can be thermally expanded during insertion at a temperature above the operating temperature of the monitor. Upon cooling intimate contact is achieved. In still another construction, the sheathed units can be installed in oversize channels and then sealed therein using solder or other suitable high temperature fillers. By combining the heater in the same sheath as the thermocouple, there is only one sheath to bring into good thermal contact with the body 16. Such combined heaters and thermocouples are known in the art.

Figure 3:
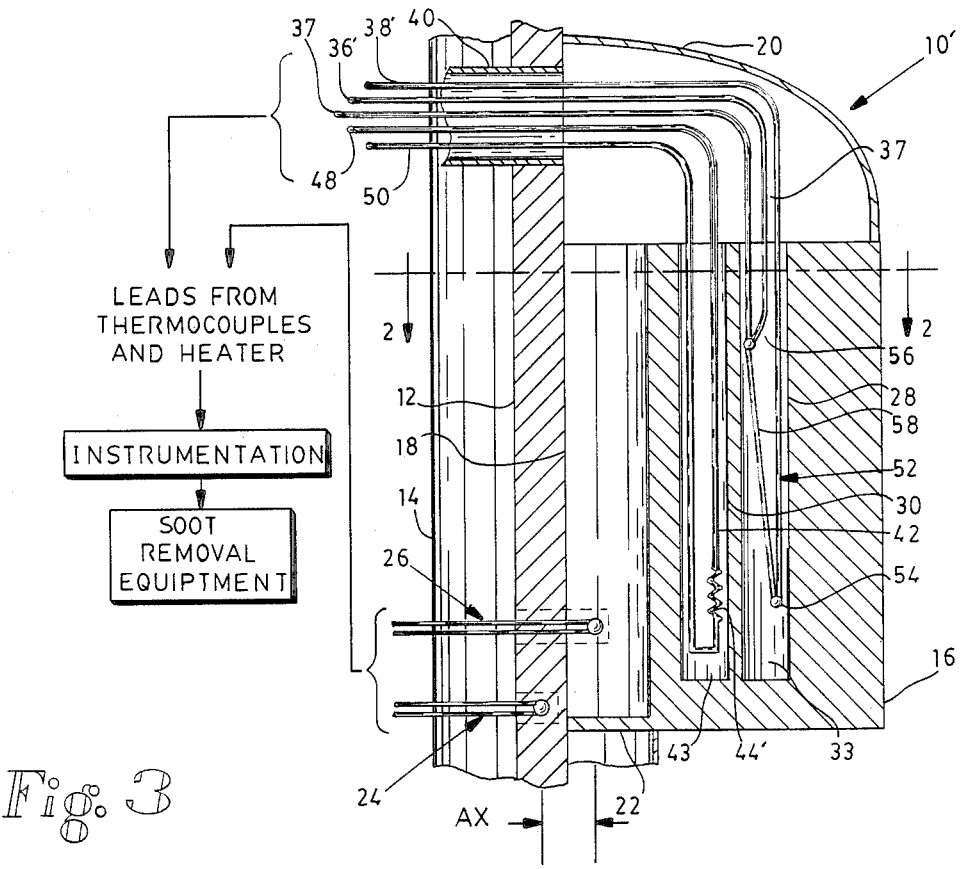
FIG. 3 is a longitudinal cross-section of another embodiment of the present invention.

A slightly modified embodiment of the present invention is illustrated in FIG. 3. The only substantial change from FIG. 1 is in the choice of the thermocouple proximate the heater 42; thus, essentially all other components are designated with the same numerals. In this embodiment, a three wire thermocouple 52 is positioned within channel 28; this thermocouple having a hot junction 54 proximate heater portion 44' joined to a cold junction 56 with lead 58, with the cold junction positioned well away from the heater portion 44'. The output of thermocouple 52 appears on leads 36', 37, and 38'. The advantage of this construction is the compensation that is provided for effects of fluctuations in temperature throughout the boiler. Although the temperature at the monitor does fluctuate, the fluctuation affects both the hot and cold junction similiarly with little change in the output signal from the three wire thermocouple.

In the utilization of the present invention, a plurality of the units such as shown in FIG. 1 are located in those portions of a boiler/steam generator wherein prior experience has shown excessive accumulation of slag or other deposits. The units are mounted on the water wall, on the side facing the flame of the steam generator, so as to be subjected to the same flame-side conditions as the water tubes 14, 14', etc. There will be heat flow through the body 16 in a direction indicated by the arrows 53, 55. Thermocouples 24, 26 of each of the units connect to appropriate circuitry so that the temperature of the water wall 12 and the body 16 of the monitor are recorded continuously (or intermittently if desired). When slag forms upon the exterior of the body 16, which accumulation would be similar to that on the exterior of the water tubes 14, the amount of heat transferred to the body 16 from the boiler flame decreases. This decrease would be shown, for example, in the output of the aforementioned thermocouples 24, 26. Furthermore, if the spacing ($\Delta x$ in FIGS. 1 and 3) is known, the instantaneous heat flux (Q/A) at the monitor can be obtained using the equation:

$$Q/A = \frac{k}{\Delta x} (T_{26} - T_{24});$$

where k is the thermal conductivity of the body material, and $T_{26}$ and $T_{24}$ are the temperatures as measured by thermocouples 26, 24, respectively.

A similar signal decrease would be shown in the output of the junction 34 of thermocouple 32. The reduction in time averaged temperature at any of the junctions at nominal steady state boiler condition is due to a decrease in heat transfer from the boiler flame to the body. In addition, when the heater is energized, the rate of change of the output signal of the thermocouple 32 is indicative of the condition of the exterior of the body. Slag deposits reduce the energy radiated away from the body 16 and thus cause the thermocouple temperature to rise more rapidly.

In addition to noting actual differences in temperature readings as an indication of slag buildup, the device further provides a way of determining the degree of such buildup. For example, when the heater 42 is operated, a certain portion of the heat produced thereby at portion 44 will be radiated from the device in a given period of time. When the slag buildup becomes excessive, the rate of heat transfer is reduced. The amount of reduction appears in the form of a change in the time constant of the temperature measurement as determined by the thermocouple 32.

Figure 4:
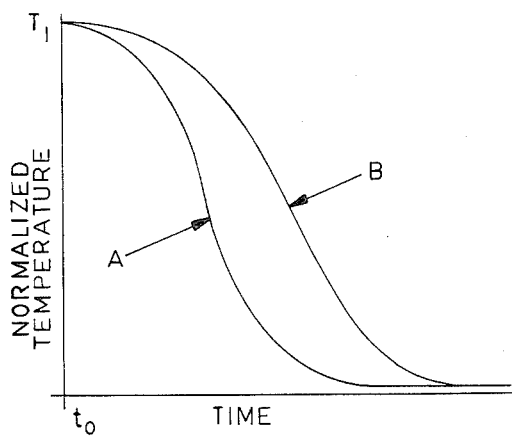
FIG. 4 is a plot of temperature (as measured by a temperature sensor proximate the heater) versus time showing the effect of slag buildup upon the time constant determined with the sensor of FIG. 1, for example.

FIG. 4 illustrates this change in time response of thermocouple 32 as a function of the slag buildup. At the time the heater unit 42 is de-energized, the thermocouple junction 34 provides a signal corresponding to $T_1$. When the present monitor is substantially clean (no slag buildup), the monitored temperature will drop following Curve A due to radiation from the surface of the body. However, when slag is present, the temperature declines more slowly following a curve such as Curve B due to loss of radiation from the body. The greater the buildup, the more separation there will be between Curves A and B. A similar relationship of temperature vs. time can be seen immediately after energizing the heater.

Thus, the heater can be used to not only establish that the thermocouple is measuring a correct temperature, but also the amount of slag buildup by this change in time constant.

When it is determined from a change in the time response (as from curve A to curve B), that the heat transfer has been reduced a selected amount due to the slag buildup, operation of soot removers 62 (see FIG. 3) can be initiated manually or automatically, knowing that their operation is occurring at the most efficient time. The outputs of the thermocouples can be utilized to determine when an optimum amount of slag or other deposits have been removed from the exterior of the unit 10 and the corresponding tubes 14.

The instrumentation 60 illustrated in block form on FIG. 3 is standard circuitry known to those versed in the art. It includes, for example, circuits for providing power to the heater 42 during selected intervals of time to study the time response of the thermocouple 53 (or 32). Also included are standard thermocouple circuits for receiving the voltage signals from thermocouple 52 (or 32), 24 and 26, and for converting these signals into temperature read-out values. The instrumentation additionally determines from the thermocouple output signals a temperature rate-of-change value for ascertaining the degree of slag accumulation. All of these functions of the instrumentation are inferred in the above-described discussion and the figures.

As indicated above, the present invention is not limited to the use of thermocouples for temperature measurement. Accordingly, other types of sensors can be used, such as resistance thermometers.

From the foregoing, it will be recognized by those versed in the art that a monitor has been provided for determining the degree of slag buildup within the fire box of a steam generator or the like. The time constant of the measuring thermocouple can be used to ascertain the degree of slag buildup. It will be apparent to those versed in the art that this monitor also can be used for determining the quality of heat transfer at many types of surfaces.

The examples of embodiments given herein are not given as a limitation of the present invention. Rather it is intended that the invention is only to be limited by the attached claims and equivalents thereof when read in combination with the Specification.

We claim:

1. A monitor system for determining the change in heat transfer to a water wall, containing a plurality of water tubes, of a steam generator due to a buildup of slag and other constituents of fly ash produced by a flame in said generator, which comprises:

a body member for positioning proximate said water tubes, said body member having a hollow portion and defining a central portion facing said flame and a pair of leg portions, said leg portions for attachment to said water wall, said central portion being thermally decoupled from said water wall, said central portion provided with first and further channels in close proximity;

a temperature sensor having a temperature sensitive portion positioned within said first channel of said central portion of said body member, said temperature sensor being in thermal contact with said body member and having output leads;

a heater unit positioned within said further channel of said central portion of said body member, said heater unit being in thermal contact with said body member and having a high temperature portion positioned proximate said temperature sensitive portion of said temperature sensor, said heater unit having input leads; and instrumentation means connected to said output leads of said temperature sensor and to said input leads of said heater unit, said instrumentation means providing a selected current to said heater unit during selected time intervals to establish a selected temperature at said high temperature portion, and further providing a measure of a time constant of a rate of change of a signal carried by said output leads of said temperature sensor, said time constant varying in proportion to the buildup of slag and other constituents of fly ash on said body member.

2. The device of claim 1 wherein said temperature sensor is a three wire thermocouple having a hot junction positioned proximate said high temperature portion of said heater unit, and a cold junction spaced away from said high temperature portion of said heater unit.

3. The device of claim 1 wherein said temperature sensor is a resistance thermometer.

4. The device of claim 1 further comprising a second temperature sensor located in said water wall and a third temperature sensor located in one of said legs of said body member and spaced a selected distance from said second temperature sensor, with output leads from said second and third temperature sensors connected to said instrumentation means, said instrumentation means further providing for a measure of a difference between a signal carried by said output leads of said second temperature sensor and a signal carried by said output leads of said third temperature sensor, and calculating a heat flux value from said difference.

5. The monitor system of claim 1 wherein said hollow portion of said body member is filled with air whereby said central portion is thermally decoupled from said water wall.

6. A monitor system for determining the degree of buildup of slag and other constitutents of fly ash from a flame within a steam generator, said steam generator having a water wall containing a plurality of water tubes, which comprises:

a semi-cylindrical body member for positioning within said steam generator at a position proximate said water tubes, said body member having a hollow portion and defining a central portion and a pair of leg portions, said leg portions for attachment to said water wall, said central portion facing said flame and being thermally decoupled from said water wall, said central portion being provided with first and second channels in close proximity;

a three wire thermocouple having a hot junction and a cold juunction positioned within said first channel in thermal contact with said body member, said three wire thermocouple having output leads;

a heater unit positioned within said second channel in thermal contact with said body member, said heater unit having a high temperature portion positioned proximate said hot junction of said thermocouple, said heater unit having input leads; and instrumentation means connected to said output leads of said temperature sensor and to said input leads of said heater unit, said instrumentation means providing a selected current to said heater unit during selected time intervals to establish a selected temperature at said high temperature portion, and for determining a time constant of a rate of change of a signal carried by said output leads of said temperature sensor after initiation or cessation of said current to said heater unit, said time constant varying in proportion to the degree of buildup of slag and other constituents of fly ash from said flame on said body member.

7. The device of claim 6 further comprising a first two wire absolute thermocouple located in said water wall and a second two wire absolute thermocouple located within one of said legs of said body and spaced a selected distance from said first two wire absolute thermocouple with output leads from said thermocouple in said wall and said thermocouple in said leg of said body being connected to said instrumentation means, said instrumentation means further providing a measure of a difference in a signal carried by said leads of said first two wire absolute thermocouple and a signal carried by said leads of said second two wire absolute thermocouple, and calculating a heat flux value from said difference.

8. The device of claim 6 further comprising soot removal apparatus, said instrumentation means energizing said soot removal apparatus when said time constant exceeds a preselected value corresponding to excessive buildup of slag within said steam generator.

9. The monitor system of claim 6 wherein said hollow portion of said body member is filled with air whereby said central portion is thermally decoupled from said water wall.

10. A monitor system for measuring the presence and relative amount, of deposits on the surface of a water wall facing a flame of a coal fired stream generator, such deposits formed by constituents of fly ash as a result of burning of said coal, which comprises:

a semi-cylindrical body member facing said flame, said body member having a hollow portion and defining a central portion and a pair of leg portions, said leg portions attached to said water wall, said central portion being provided with first and further parallel channels in close proximity extending along said body member, said hollow portion of said body member being filled with air whereby said central portion is thermally decoupled from said water wall;

a metallic sheathed resistance heater positioned in said first channel and thermally coupled to said body member, said resistance heater provided with input current leads;

a first metallic sheathed temperature sensor positioned in said further channel and thermally coupled to said body member, said temperature sensor provided with output signal leads;

instrumentation means connected to said leads of said heater and leads of said temperature sensor, said instrumentation means providing a selected current through said input leads to said heater during selected time intervals to produce a selected temperature at said heater, said instrumentation means further providing a measure of a time constant of a rate of change of a temperature related signal carried on said output leads of said temperature sensor after initiation or cessation of current to said heater, said time constant increasing as said deposits increase on said water wall, whereby said instrumentation means initiates an operation signal when said time constant exceeds a selected value; and soot removal means connected to said instrumentation means, said soot removal means activated upon receipt of said operation signal when said time constant exceeds said selected value for removal of said deposits causing said increased time constant.

* * * * *